(12) United States Patent
Wells et al.

(10) Patent No.: US 11,529,503 B2
(45) Date of Patent: *Dec. 20, 2022

(54) APPARATUS AND METHODS FOR CONTROLLING TISSUE OXYGENATION FOR WOUND HEALING AND PROMOTING TISSUE VIABILITY

(71) Applicant: ELECTROCHEMICAL OXYGEN CONCEPTS, INC., San Antonio, TX (US)

(72) Inventors: Michael C. Wells, San Antonio, TX (US); Mark Parker, Houston, TX (US); Daniel J. Clarius, Missouri City, TX (US); Andrew Parker, Missouri City, TX (US); Faraidoon Pundole, Sugar Land, TX (US); Tom Woods, Friendswood, TX (US); Mark Niederauer, San Antonio, TX (US); James P. Daley, San Antonio, TX (US)

(73) Assignee: ELECTROCHEMICAL OXYGEN CONCEPTS, INC., San Antonio, TX (US)

( * ) Notice: Subject to any disclaimer, the term of this patent is extended or adjusted under 35 U.S.C. 154(b) by 954 days.

This patent is subject to a terminal disclaimer.

(21) Appl. No.: 16/298,294

(22) Filed: Mar. 11, 2019

(65) Prior Publication Data

US 2019/0201672 A1 Jul. 4, 2019

Related U.S. Application Data

(63) Continuation of application No. 14/961,587, filed on Dec. 7, 2015, now Pat. No. 10,226,610, which is a (Continued)

(51) Int. Cl.
*A61M 35/00* (2006.01)

(52) U.S. Cl.
CPC ..... *A61M 35/30* (2019.05); *A61M 2202/0208* (2013.01); *A61M 2205/3324* (2013.01);
(Continued)

(58) Field of Classification Search
CPC .......... A61M 35/30; A61M 2202/0208; A61M 2205/3324; A61M 2205/3334; A61M 2205/3344; A61M 2205/3368
See application file for complete search history.

(56) References Cited

U.S. PATENT DOCUMENTS

| | | |
|---|---|---|
| 3,489,670 A | 1/1970 | Maget |
| 5,578,022 A | 11/1996 | Scherson et al. |

(Continued)

FOREIGN PATENT DOCUMENTS

| | | |
|---|---|---|
| CN | 102083478 A | 6/2011 |
| CN | 102112171 A | 6/2011 |

(Continued)

OTHER PUBLICATIONS

Office Action dated Dec. 9, 2020 issued in related Japanese patent application No. 2018-549144 (11 pages).

(Continued)

*Primary Examiner* — Jessica Arble
(74) *Attorney, Agent, or Firm* — Haynes and Boone, LLP; William B. Nash

(57) ABSTRACT

A wound treatment system includes a housing. A processor is located in the housing. A pressure monitoring system is coupled to the processor. A power delivery system is located in the housing and coupled to the processor. An oxygen concentrator is located in the housing and coupled to the power delivery system. The oxygen concentrator includes a plurality of oxygen outlets. The processor is configured to receive pressure information from the pressure monitoring system that is indicative of a pressure in a restricted airflow (Continued)

enclosure provided by a dressing and located adjacent a wound site; and use the pressure information to control the power provided from the power delivery system to the oxygen concentrator in order to control an oxygen flow created by the oxygen concentrator and provided through one of the plurality of oxygen outlets to the restricted airflow enclosure.

20 Claims, 12 Drawing Sheets

Related U.S. Application Data continuation-in-part of application No. 12/738,905, filed as application No. PCT/US2009/002523 on Apr. 23, 2009, now Pat. No. 9,730,838, which is a continuation of application No. 12/288,873, filed on Oct. 24, 2008, now Pat. No. 8,287,506.

(60) Provisional application No. 61/000,695, filed on Oct. 26, 2007.

(52) U.S. Cl.
CPC .......... *A61M 2205/3334* (2013.01); *A61M 2205/3344* (2013.01); *A61M 2205/3368* (2013.01)

(56) References Cited

U.S. PATENT DOCUMENTS

| | | | |
|---|---|---|---|
| 5,788,682 A | 8/1998 | Maget | |
| 6,010,317 A | 1/2000 | Maget et al. | |
| 6,071,267 A | 6/2000 | Zamierowski | |
| 6,171,368 B1 | 1/2001 | Maget et al. | |
| 6,458,109 B1 | 10/2002 | Henley et al. | |
| 7,014,630 B2 | 3/2006 | Rosati | |
| 7,263,814 B2 | 9/2007 | Rosati | |
| 7,316,857 B1 | 1/2008 | Swanson et al. | |
| 7,322,971 B2 | 1/2008 | Shehada | |
| 7,368,005 B2 | 5/2008 | Bliss et al. | |
| 8,287,506 B2 * | 10/2012 | Wells | A61P 17/02 604/23 |
| 9,730,838 B2 * | 8/2017 | Wells | A61P 17/02 |
| 10,226,610 B2 * | 3/2019 | Wells | A61M 35/30 |
| 10,632,018 B2 * | 4/2020 | Wells | A61M 35/00 |
| 10,702,686 B2 * | 7/2020 | Niederauer | A61M 35/30 |
| 2002/0198504 A1 | 12/2002 | Risk, Jr. et al. | |
| 2003/0083610 A1 | 5/2003 | McGrath et al. | |
| 2006/0225737 A1 | 10/2006 | Lobbi | |
| 2006/0287632 A1 | 12/2006 | Sarangapani | |
| 2007/0118096 A1 * | 5/2007 | Smith | A61B 5/445 604/541 |
| 2007/0299412 A1 | 12/2007 | Vogel | |
| 2008/0003299 A1 | 1/2008 | Trotter et al. | |
| 2008/0086072 A1 | 4/2008 | Bonutti et al. | |
| 2008/0234616 A1 | 9/2008 | Shives et al. | |
| 2008/0308100 A1 | 12/2008 | Pujol et al. | |
| 2009/0112170 A1 | 4/2009 | Wells et al. | |
| 2011/0034861 A1 | 2/2011 | Schaefer | |
| 2011/0054388 A1 | 3/2011 | Wells et al. | |
| 2011/0130712 A1 | 6/2011 | Topaz | |
| 2013/0144227 A1 | 6/2013 | Locke et al. | |
| 2015/0290364 A1 | 10/2015 | Wall et al. | |
| 2019/0001107 A1 | 1/2019 | Niederauer et al. | |

FOREIGN PATENT DOCUMENTS

| | | |
|---|---|---|
| CN | 103347561 A | 10/2013 |
| CN | 103930138 A | 7/2014 |
| CN | 102202618 B | 9/2014 |
| JP | Sho/62-129052 | 6/1987 |
| JP | 2000-507459 | 6/2000 |
| JP | 2002-524109 | 8/2002 |
| JP | 2004-529090 | 9/2004 |
| JP | 2005-511205 | 4/2005 |
| JP | 2008-539966 | 11/2008 |
| JP | 2011-528958 T | 12/2011 |
| JP | 2012-506292 T | 3/2012 |
| WO | WO 2006/122169 | 11/2006 |

OTHER PUBLICATIONS

Office Action issued in related Chinese application No. 201680071641.3 dated May 18, 2020 (15 pages).

International Search Report and Written Opinion dated Jul. 2, 2020 issued in related PCT App. No. PCT/US2020/028312 (14 pages).

Search Report issued from Japan Patent Office (and English translation) in Japanese Patent Application 2011-533156, dated Jun. 25, 2013, 9 pages.

International Search Report and Written Opinion dated Feb. 24, 2017 issued in related PCT Application Serial No. PCT/US16/65378 (18 pages).

* cited by examiner

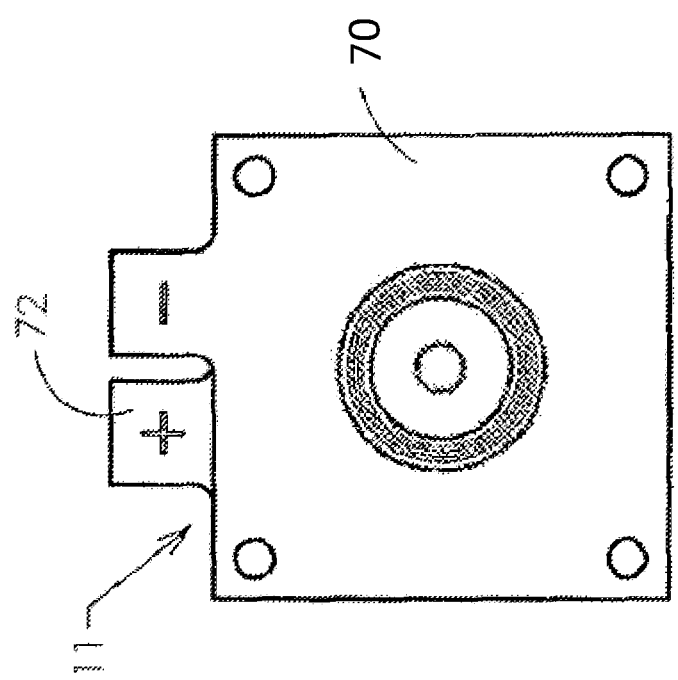

APPARATUS AND METHODS FOR CONTROLLING TISSUE OXYGENATION FOR WOUND HEALING AND PROMOTING TISSUE VIABILITY

CROSS REFERENCE TO RELATED APPLICATIONS

This application is a continuation of U.S. patent application Ser. No. 14/961,587 filed Dec. 7, 2015 (which will issue as U.S. Pat. No. 10,226,610 on Mar. 12, 2019), which is a continuation-in-part of U.S. patent application Ser. No. 12/738,905, filed Nov. 11, 2010, which is a national stage entry of PCT Application No. PCT/US09/02523, filed Apr. 23, 2009, which claims the benefit of U.S. patent application Ser. No. 12/288,873 (now U.S. Pat. No. 8,287,506), filed Oct. 24, 2008, which claims the benefit of U.S. Provisional Application No. 61/000,695, filed Oct. 26, 2007. The contents of each referenced application are hereby incorporated by reference herein.

BACKGROUND

Field

Embodiments disclosed herein relate to tissue treatment systems, specifically to tissue oxygenation systems for accelerating the healing of damaged tissue and promoting tissue viability. The tissue oxygenation system described herein may be used to treat skin ulcerations due to diabetes, venous stasis, post surgical infections, gangrenous lesions, pressure ulcers, infected residual limbs, skin grafts, burns, frostbite, and/or a variety of other wounds and bodily conditions known in the art.

When tissue is damaged, a wound results and a healing process begins. The term "wound" may include, but is not limited to, chronic wounds, traumatic wounds, surgically created wounds, and/or other wounds known in the art. Optimal metabolic function of cells to repopulate tissue in the wound requires that oxygen be available for all phases of wound healing, and the more layers of tissue that are damaged, the greater the risk for complications to occur in the wound healing process.

Difficult-to-heal wounds encounter barriers to the wound healing process and typically experience delays in one or more of the phases of wound healing. One of the most common contributing factors to venous leg ulcers, diabetic foot ulcers, and pressure ulcers experiencing delays in the healing process is the problem of chronic wound ischemia. Chronic wound ischemia is a pathological condition that restricts blood supply, oxygen delivery, and blood request for adequate oxygenation of tissue, operating to inhibit normal wound healing.

In practice the standard of care for treating difficult-to-heal wounds typically involves the use of an advanced wound dressing or combinations of advanced wound dressings that provide a dressing treatment system. An advanced dressing is positioned on the wound site and/or around the surrounding intact skin to provide a wound site enclosure. An advanced wound dressing typically includes materials having properties for promoting moist wound healing, managing wound exudate, and helping control wound bioburden. The typical material components in combination further include properties for providing limited moisture vapor permeability. The lower the dressing's moisture vapor permeability, or the more occlusive the dressing, the lower the amount of ambient air and respective oxygen that will be available to the wound bed. 100% oxygen exerts a partial pressure of 760 mm Hg. Ambient air is comprised of about 21% oxygen, thereby exerting a partial pressure of oxygen at about 159 mm Hg. A typical advanced wound dressing or wound dressing system including lower moisture vapor permeable materials impacts the available oxygen for the wound site, thereby limiting the partial pressure of oxygen at the enclosed wound site at about 10-60 mm Hg. As such, fresh air is provided to the wound site only when the dressing is changed, and a dressing may remain covering the wound site for up to seven days before a dressing change is required. The moisture vapor permeability property of an advanced wound dressing providing a reduced oxygen wound environment thereby works against the optimal metabolic function of cells to repopulate tissue in the wound, which would benefit from oxygen being available during all phases of wound healing.

Prior art methods of tissue oxygenation for difficult-to-heal wounds typically include topical hyperbaric oxygen applied intermittently or continuously. Intermittent topical hyperbaric oxygen is a method of tissue oxygenation that includes a sealed extremity or partial body chamber and a connected source of high flow, pure oxygen. The affected limb or affected body area is positioned in the sealed extremity chamber or partial body chamber so that the oxygen source supplying the chamber may provide the patient topically up to 100% oxygen at flow rates that may exceed 300 liters per hour to pressurize the interior of the chamber up to 1.05% normal atmospheric pressure, thereby increasing the available oxygen for cellular processing at the affected wound site. During the oxygen application, the partial pressure of oxygen exerted inside the topical or partial body chamber may attain 798 mm Hg, and the topical hyperbaric oxygen may be applied for about 90 minutes. Prior art also teaches a plurality of methods to apply topically hyperbaric oxygen intermittently. A partial body chamber for treating sacral wounds has been described in U.S. Pat. No. 4,328,799 to LoPiano (1980), whereby oxygen is applied from a stationary supply tank into the interior of the chamber through connected tubing. A similar method of applying topical hyperbaric oxygen is described in U.S. Pat. No. 5,478,310 to Dyson-Cantwell (1995), whereby oxygen is applied from a stationary supply tank into the interior of the disposable extremity chamber through connected tubing. These and similar methods of applying intermittent topical hyperbaric oxygen are restrictive, cumbersome, can only supply oxygen to the affected area intermittently with no systemic application, and can only be applied with a minimal increase in atmospheric pressure (about 5%). Therefore the effect of the oxygen therapy on the wound tends to be minimal, which is evidenced by the lack of commercial success from topical hyperbaric oxygen extremity chambers.

Both U.S. Pat. No. 5,578,022 to Scherson (1996) and U.S. Pat. No. 5,788,682 to Maget (1998) describe disposable devices utilizing transmission of gases in ionic form through ion specific membranes to apply supplemental oxygen directly to the wound bed. These devices are described as battery powered, disposable, oxygen producing bandages and methods that are applied directly over the wound. Both devices include electrochemical oxygen generation using variations of the same 4 electron formula originally developed for NASA in U.S. Pat. No. 3,489,670 to Maget (1970). The amount of oxygen that can be applied to the wound is typically 3 milliliters per hour. Specific oxygen flow rates are generated by means of corresponding specific, preselected battery sizes and specific, prescribed amperages, and describes these disposable devices as either "on or off." The prior art also describes disposable devices without means to sense temperature changes in the wound site oxygen environment, and does not provide a means to deliver a varying or adjustable oxygen flow rate without requiring the patient to obtain and apply a new device with a new battery having a specific amperage. Additional limitations are also associated with the use of a fixed non-variable oxygen flow rate.

No prior art tissue oxygenation device provides continuous oxygen adjustability to a patient's wound(s) to create a controlled hyperoxia and hypoxia wound environment for damaged tissue to accelerate wound healing and promote tissue viability. Specifically, nothing in the prior art teaches continuous oxygen adjustability based on actual flow rate, partial pressures at the wound site, and, where beneficial, temperatures, pH values, and/or other local conditions at the wound site.

SUMMARY AND DESCRIPTION

Embodiments disclosed herein include improved tissue oxygenation devices and wound monitoring systems. Those embodiments generally comprise an oxygen delivery, microbore tube for placement at or near the wound bed, and a wound dressing covering the tubing and wound site to provide a restricted air flow enclosure. The tubing may have multiple holes at or near the distal end of the tubing, and may include a generally flat, flexible, oxygen-permeable tape or membrane section attached at the distal end of the tubing. The tubing may be flexible with a kink resistant inner lumen. The tubing may include a temperature sensor. The tubing may include a pressure sensor. The tubing may include a partial pressure of oxygen sensor. The proximal end of the tubing is connected to a source of oxygen. The proximal end of the tubing may have a port Leur-type locking mechanism for an airtight seal during application of the oxygen and for removal from the oxygen source during application of a dressing. A source of oxygen is in communication with the proximal and distal ends of the tube, and may be provided by an electrochemical oxygen concentrator supplied by alternating or direct current, and a power management device using a power management protocol. The variable electrochemical oxygen concentrator is used in accordance with the embodiments of the present disclosure by varying the oxygen flow rate to meet varying target parameters at the wound site. The oxygen flow rate is adjusted by a system that periodically or continuously monitors the wound bed pressure and, where beneficial, the temperature environment. Additionally, the system may monitor the tubing pressure and adjust the oxygen flow rate in accordance to target set points. Adjusting oxygen flow in response to monitored changes in wound site oxygen and target oxygen pressure and, where beneficial, wound site temperature, humidity, pH or perfusion, provides a controlled hyperoxia wound environment which may shorten the healing process. The present monitoring system may further provide an alarm when the pressure, temperature, humidity, pH, perfusion, or flow rates have gone out of range.

In some situations, excessive oxygen pressure (i.e., greater than 22 mm of Hg) can occlude arterial circulation and lead to decreased local tissue circulation and, in some cases, local tissue damage. Embodiments of the device design may address how the device controls oxygen pressure such that pressures do not exceed a safe limit. Unlike a conventional topical oxygen chambers for extremities, the present system does not create a sealed, oxygen rich environment inside a chamber in which a patient's limb is inserted. Instead, oxygen may be generated by a Proton Exchange Membrane within the portable device and delivered to the wound site via micro-bore tubing at a rate of 3 ml/hr to 100 ml/hr. Because the wound site is covered only by occlusive wound dressing instead of the entire limb being inserted into a sealed chamber, such oxygen pressure at the site and around the limb may never exceed normal atmospheric pressure.

In some embodiments, the device may have a backlight display terminal or touch screen liquid crystal display, a data input key pad or device function control buttons, a wound or housing temperature monitoring system, a wound or device humidity monitoring system, a battery and oxygen pressure alarm system, a digital camera, a patient data input and memory system, a data port, wireless data access, and/or the other components discussed below.

BRIEF DESCRIPTION OF THE DRAWINGS

A more complete understanding of the present disclosure and advantages thereof may be acquired by referring to the following description taken in conjunction with the accompanying figures, wherein:

FIG. 6 is a top plan view illustrating an embodiment of the electrolyzer/concentrator that may be used in the tissue oxygenation system of FIG. 1.

Figure 1:
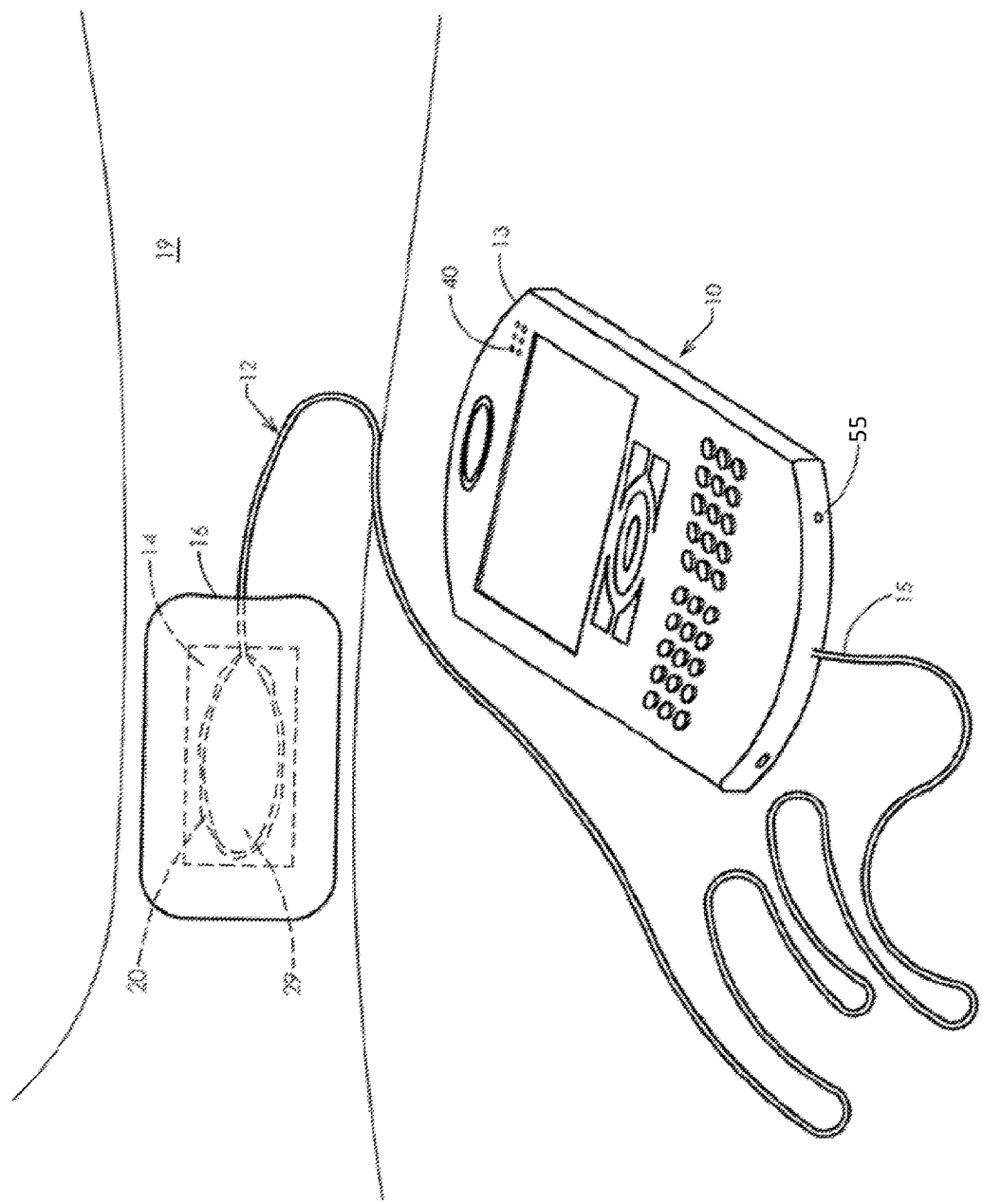
FIG. 1 is a perspective view illustrating an embodiment of a tissue oxygenation system.

While the embodiments of the present disclosure are susceptible to various modifications and alternative forms, specific exemplary embodiments thereof have been shown by way of example in the drawings and are herein described in detail. It should be understood, however, that the description herein of specific embodiments is not intended to limit the present disclosure to the particular forms disclosed and, rather, the intention is to cover all modifications, equivalents, and alternatives falling within the spirit and scope of the present disclosure as defined by the appended claims.

DETAILED DESCRIPTION

Several embodiments of tissue oxygenation systems for promoting the healing of damaged tissue and tissue viability will now be described in detail with reference to the figures.

FIG. 1 is a perspective view of several components of the tissue oxygenation system of the present disclosure providing oxygen to a wound. The illustrated embodiment includes a monitoring unit 10, an electrochemical oxygen concentrator 11, oxygen delivery tubing 12, a moisture absorbent dressing 14, and vapor permeable dressing 16. The oxygen delivery tubing 12 may be connected (at the proximal end 15 of the relatively long, kink-resistant tubing illustrated in FIG. 1) to the monitoring unit 10. In an embodiment, the monitoring unit 10 is provided in a relatively small, light-weight housing that is portable and may be discretely worn by a patient in a pocket, attached to a belt, and/or otherwise carried by the patient in various manners known in the art.

The monitoring unit 10 may include, within the housing 13, any or all of a microprocessor 58 (see FIGS. 4 and 5), a power management system 52, one or more pressure sensors 30a or pressure sensor interfaces, one or more temperature sensors 32a or temperature sensors interfaces, one or more flow rate sensors 54 or flow rate sensor interfaces, an input port 62, and a user entry port 66. The monitoring unit 10 may further include, within the housing 13, any or all of one or more pH sensors 34a or pH sensor interfaces, one or more perfusion sensors 36a or perfusion sensor interfaces, and one or more humidity sensors 38a or humidity sensor interfaces. The electrochemical oxygen concentrator 11 may be disposed within the housing 13. The microprocessor 58 may function to control power, collect various readings from flow rate sensor(s) 54, pressure sensor(s) 30a, pH sensor(s) 34a, perfusion sensor(s) 36a, humidity sensor(s) 38a, and temperature sensor(s) 32a, either included in the housing 13 or coupled to the corresponding interfaces in the housing 13, control ionic purification of ambient air by the electrochemical oxygen concentrator 11 for delivery to the tubing 12, and provide information on the informational display of the monitoring unit 10. The microprocessor 58 is capable of receiving data through the user entry port 66 and the input port 62, wirelessly via BLUETOOTH®, WiFi®, and/or other wireless technologies known in the art, and/or using other communication system, with that data including information related to specific patients, re-programming information if there is a system malfunction with the device, and/or any other information that would be apparent to one of skill in the art in possession of the present disclosure.

Figure 1A:
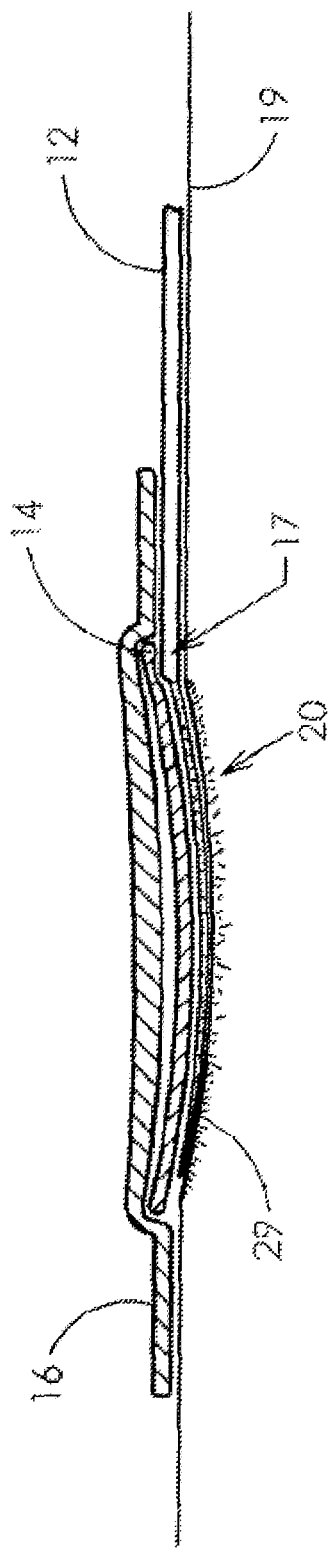
FIG. 1A is a front view illustrating an embodiment of the tissue oxygenation system of FIGS. 1 and 1A being used to treat multiple wounds on a patient.
Figure 2:
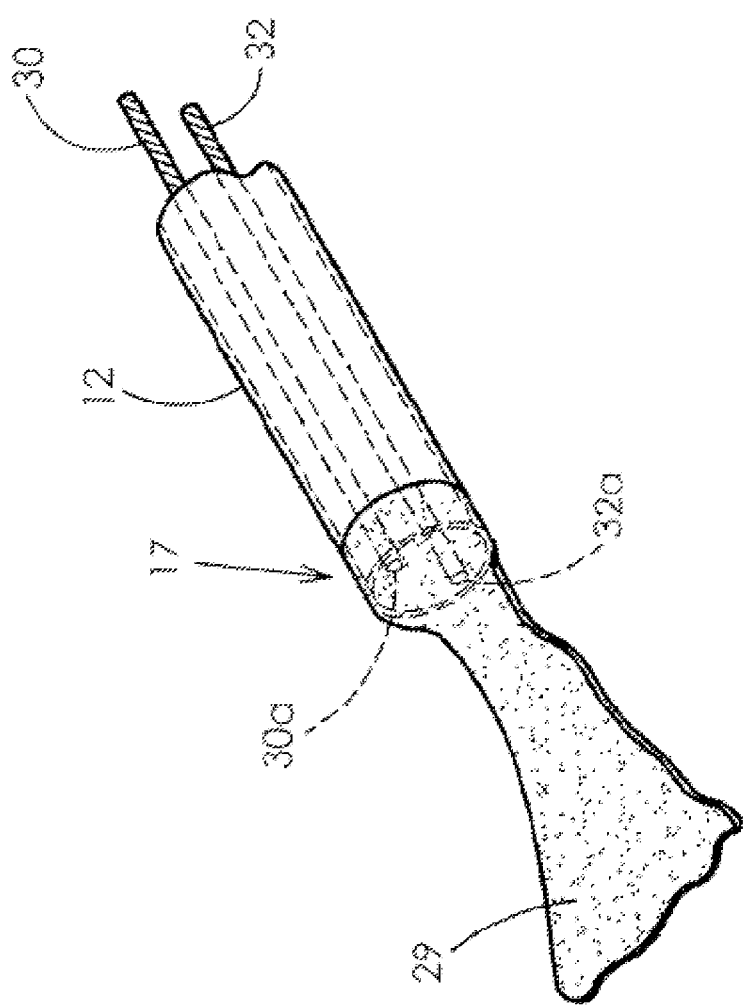
FIG. 2 is a side perspective view illustrating an embodiment of the distal end of the oxygen delivery tubing of FIG. 1A showing a generally flat, flexible, oxygen-permeable tape or membrane section affixed to the oxygen delivery tubing.

As may be further seen in FIGS. 1A and 2, a distal end 17 of the tubing 12 may include or be coupled to a soft, flexible, oxygen permeable tape or membrane section 29 that may be placed on or near damaged tissue or wound site 20 on a patient's limb 19, and covered with a moisture absorbent dressing 14, which is further covered by a reduced vapor pressure, permeable, occlusive dressing 16.

Figure 1B:
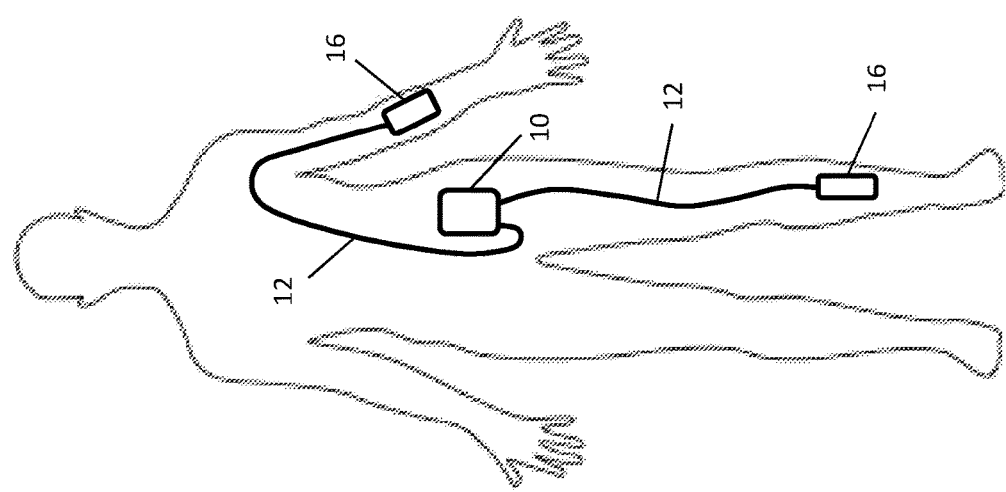
FIG. 1b is a cross section view illustrating an embodiment of a wound site showing a distal end of oxygen delivery tubing that may be used in the tissue oxygenation system of FIG. 1.

In an embodiment, oxygen may be delivered to the wound site 20 through kink-resistant tubing 12 that is connected at its proximal end 15 to the outlet of the oxygen concentrator in the housing 13 of the monitoring unit 10. Furthermore, in some embodiments, the oxygen concentrator in the housing 13 of the monitoring unit 10 may include a plurality of oxygen outlets, and a plurality of the kink-resistant tubing 12 may be connected at their proximal ends 15 to respective outlets of the oxygen concentrator, with their respective distal ends 17 placed on or near a plurality of different damaged tissue or wound sites 20 on a patient and covered by a reduced vapor pressure, permeable, occlusive dressing 16, as illustrated in FIG. 1B. While only two wounds sites on the patient are illustrated as being treated in FIG. 1B, one of skill in the art in possession of the present disclosure will recognize that any number of wounds may be treated in a similar manner for example, by increasing the oxygen output of the oxygen concentrator, providing more oxygen concentrators in the housing 13 of the monitoring unit 10, etc.

As illustrated in FIG. 2, in an embodiment, on the distal end 17 of each tubing 12, a soft, flexible oxygen-permeable flat tape or membrane 29 may be connected. Sensor wires 30 and 32 may extend through the lumen of each tubing 12 to communicate with any of the sensors or sensor interfaces included in the housing 13 of the monitor unit 10 discussed above. For example, the sensor wires 30 and 32 may communicate with temperature sensor(s) 32, oxygen partial pressure sensor(s) 30, flow rate sensor(s) 54, humidity sensor(s) 38a, pH sensor(s) 34a, perfusion sensor(s) 36a, and/or other sensors disposed at each wound site and provide that information to the microprocessor 58. In other embodiments, the sensor wires may be eliminated and temperature, pressure, flow rate, pH, perfusion, humidity, and/or other wound environment measurements may be measured within the monitor unit housing at each outlet of the oxygen concentrator.

Figure 2A:
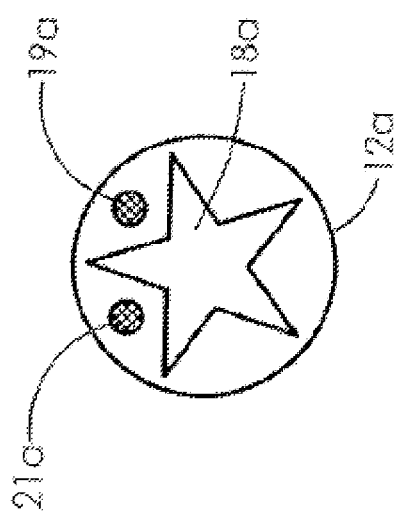
FIG. 2A is an end view illustrating an embodiment of the oxygen delivery tubing of FIG. 1A.

As illustrated in FIG. 2A, in some embodiments tubing 12a may include several lumens, sensors, and/or other subsystems as may be required to effectively monitor wound treatment. Specifically, FIG. 2A illustrates an end view of the tubing 12a, and depicts a tubing 12A with a length capable of connecting to the output side of any of the outlets of the electrochemical oxygen concentrator 11 housed within the monitoring unit 10. Such tubing lengths allow the monitoring unit to be worn discreetly while oxygen is continuously delivered to the wound site 20. An inner lumen or bore 18a of the tubing may be provided with the star-like configuration of FIG. 2A to prevent kinking of the tubing and/or enable oxygen flow when the tubing 12a is bent, although other configurations of the lumen 18a may provide similar benefits. An oxygen partial pressure sensor 19a that may be positioned at or near the wound site may be disposed within the tubing 12A and be in communication with a pressure monitoring system and/or microcontroller to allow for oxygen flow rate adjustment, visual pressure display, out-of-range alarms, and/or other benefits that would be apparent to one of skill in the art. A temperature sensor 21a that may also be positioned at or near the wound site may be disposed within the tubing 12a and be in communication with a temperature monitoring system and/or microcontroller to allow for visual display of temperature, an out-of-range alarm, to allow for oxygen adjustment via the microprocessor 58 as is appropriate, and/or to provide other benefits that would be apparent to one of skill in the art. Furthermore, the pH sensor, perfusion sensor, and/or humidity sensor that may also be positioned at or near the wound site may be similarly disposed within the tubing 12a and in communication with a pH monitoring system, perfusion monitoring system, humidity monitoring system, and/or microcontroller to allow for visual display of pH, perfusion, relative humidity, out-of-range alarms, to allow for oxygen adjustment via the microprocessor 58 as is appropriate, and/or to provide other benefits that would be apparent to one of skill in the art.

Figure 3:
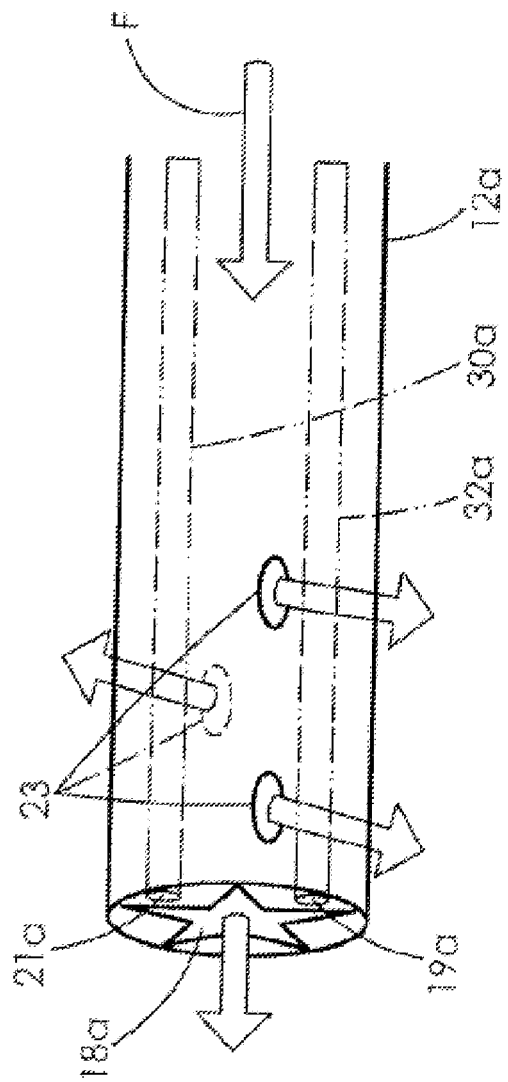
FIG. 3 is side elevation view illustrating an embodiment of the distal end of the oxygen delivery tubing of FIG. 2A.

FIG. 3 is a side view of an embodiment of the distal end of the tubing 12a, which may include a plurality of holes 23 formed along the side of the distal end of the tubing 12a to aid in the delivery of oxygen to the wound. In use, the oxygen may be provided in a flow F through the tubing 12a to the wound site and may enter the wound bed through the multiple holes 23. The oxygen may also flow through the distal end of star shaped lumen 18a, but in some embodiments the multiple holes at the distal end of the tubing 12a may allow for improved flow of oxygen to the wound site 20.

FIG. 1A illustrates a wound site 20, with the distal end 17 of the oxygen delivery tubing 12 having the oxygen distribution tape 29 placed over or near the wound site 20, although in some embodiments the tape 29 may be placed centrally on the wound site for optimal delivery of oxygen to the damaged tissue. In some embodiments, the wound may be saturated with nearly 100% O2. A moisture absorbent dressing 14 may be placed at the wound site to cover the tape end of the oxygen delivery tubing 12 and wound site. One skilled in the art in possession of the present disclosure will appreciate that a variety of moisture absorbent dressings that provide the typical standard of care protocol for a difficult-to-heal wound may be utilized with the oxygen delivery tubing 12 as discussed above. A reduced moisture vapor permeable dressing 16 may then be used to cover the moisture absorbent dressing 14, the tape end of the tubing 12, and the wound site 20 in order to create a restricted airflow enclosure. In some embodiments, the reduced moisture vapor permeable dressing 16 may be transparent and may be considered an occlusive dressing. The occlusive dressing may operate to trap the oxygen over the wound site to create and maintain oxygen rich environment. In some embodiments, the local partial pressure of oxygen at the wound site 20 may be increased from a low range of 10 to 60 mm Hg to an oxygen rich environment range of 200 to 760 mm HG, and that increased available oxygen may be metabolized at the cellular level to stimulate an increase in growth factors, epithelialization, granulation tissue, glycosaminoglycan production, collagen synthesis, and/or other wound healing factors known in the art. In an embodiment, the oxygen partial pressure at the wound site may be communicated to the pressure monitoring system and/or microprocessor in the housing 13. The oxygen partial pressure sensor may supply data to the microprocessor 58 that the microprocessor 58 may use to control the power flow (amperage) to the concentrator 11, which may in turn cause the concentrator to increase or decrease its production of O2 to change the O2 flow rate to the wound site. In some embodiments, the oxygen partial pressure sensor may be conductivity sensor, but other systems for measuring this pressure may be utilized while remaining within the scope of the present disclosure.

Figure 4:
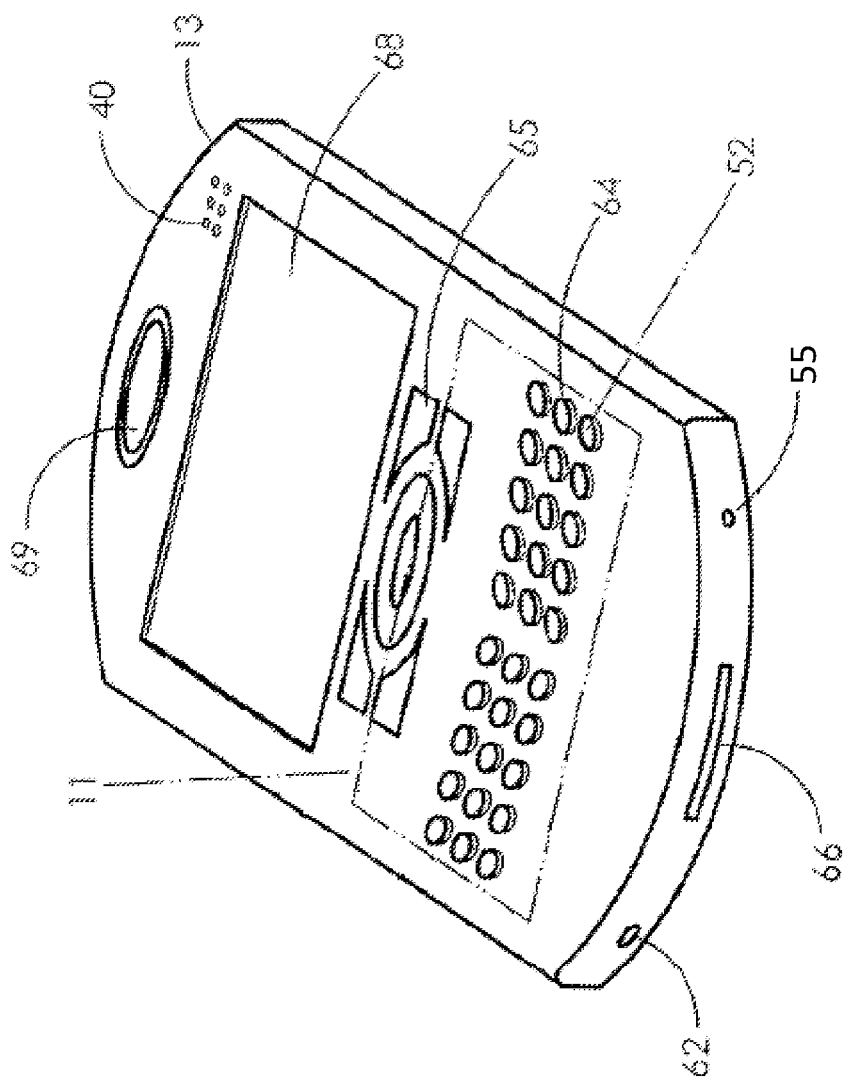
FIG. 4 is a perspective view illustrating an embodiment of a handset that may be used in the tissue oxygenation system of FIG. 1.
Figure 5:
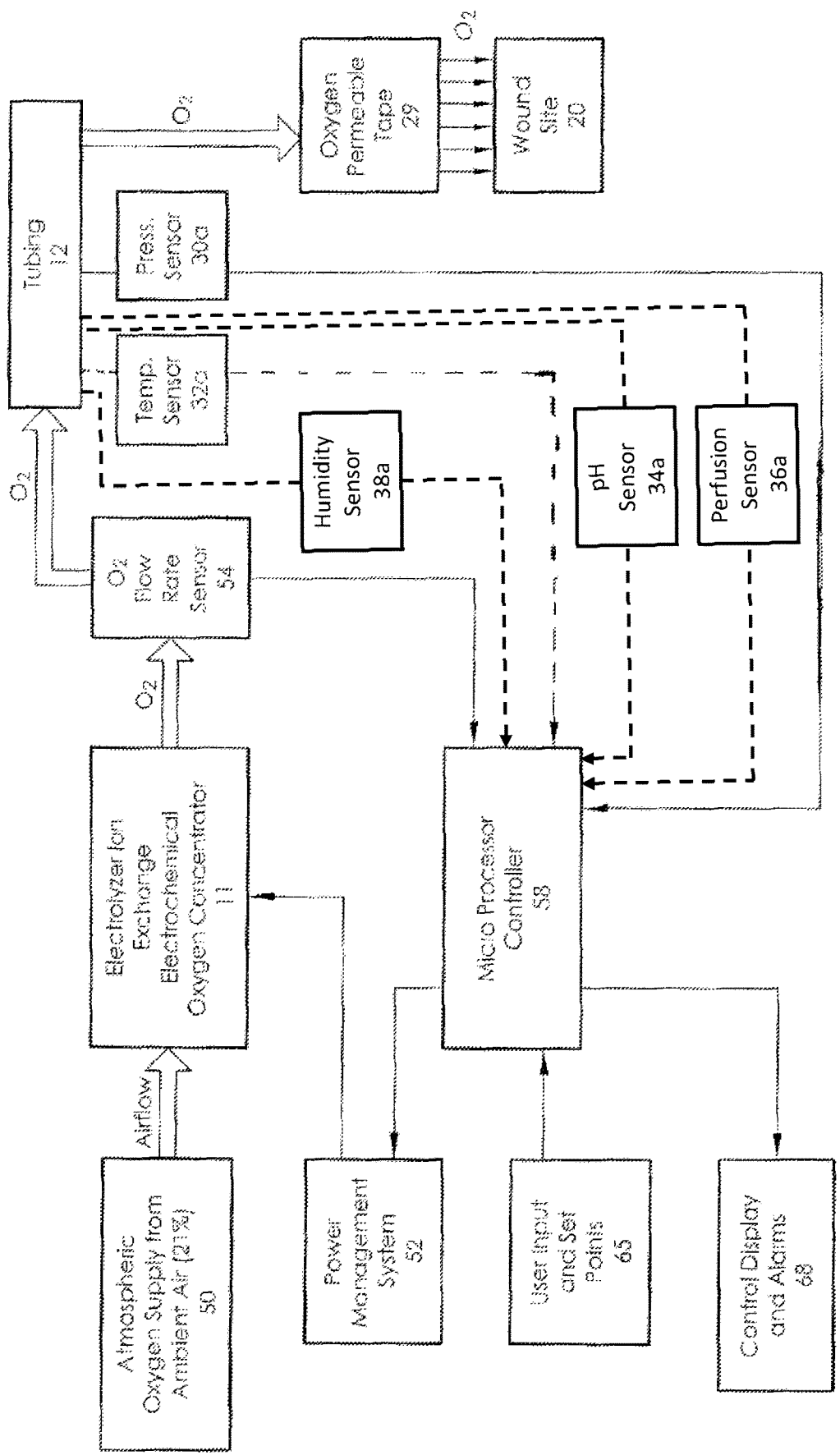
FIG. 5 is a schematic view illustrating an embodiment of the tissue oxygenation system of FIG. 1.

FIG. 4 is a perspective view of a handset that may house the components of the tissue oxygenation system of the present disclosure, while FIG. 5 is a schematic view of those components. In use, the monitor housing 13 may draw ambient air 50 with about 21% oxygen through the air inlet 40 by means of an electrochemical process. The ambient air 50 may then pass through an ion exchange oxygen concentrator 11, which operates to concentrate the oxygen in the ambient air 50 to create an airflow that is 99% pure oxygen. The power management system 52 may control the electrical current supplied to the ion exchange oxygen concentrator 11, thereby making the oxygen flow rate conform to the amount of current supplied to the ion exchange oxygen concentrator 11, i.e., increasing electrical current will increase the electrochemical process and thereby increases the respective oxygen flow rate to the wound site 20, and decreasing the electrical current will decrease the electrochemical process thereby decreasing the respective oxygen flow rate to the wound site. In some embodiments, the power management system 52 may include lithium batteries (for example, 3.7 v) and a regulator that operates to vary the current over a range of approximately 20 milliamps to approximately 140 milliamps, while in other embodiments, that range may be approximately 7 milliamps to approximately 70 milliamps. This range of current variation may result in O2 flow rates in the range between approximately 3.0 milliliters/hour to approximately 20.0 milliliters/hour in some embodiments, while in other embodiments that range may be between approximately 3.0 milliliters/hour to approximately 10.0 milliliters/hour.

The concentrated O2 then exits the housing through the oxygen delivery port 55. The proximal end 15 of the oxygen delivery tubing 12 is connected with an oxygen delivery port 55 with Leur-type locking fitting, or other fitting known in the art, to maintain an airtight seal with the tubing 12 and allows the tubing 12 to deliver that concentrated O2 to the wound site.

As illustrated in FIGS. 2 and 5, the pressure sensor 30a or 19a and, in some embodiments, the temperature sensor 32a/21a in the tubing 12 or 12a are in communication with the microprocessor 58. In addition, a pH sensor 34a, a perfusion sensor 36a, and/or a humidity sensor 38a may also be in communication with the microprocessor 58. The microprocessor 58 may communicate with the power management system 52 to adjust the oxygen flow rate (sensed by sensor 54) to the wound site per programmed algorithms to optimally meet changes in the patients oxygen wound healing requirements. In one embodiment, if a plurality of tubing 12 or 12a is connected between the oxygen concentrator and multiple wound sites (as illustrated in FIG. 1B, the microprocessor 58 may communicate with the power management system 52 to adjust the oxygen flow rates (sensed by respective sensors 54) to each individual wound site per programmed algorithms to optimally meet changes in the patient's oxygen wound healing requirements for each wound, which may be different and thus may require different oxygen flow rates and/or other treatment characteristics that would be apparent to one of skill in the art in possession of the present disclosure.

Figure 6A:
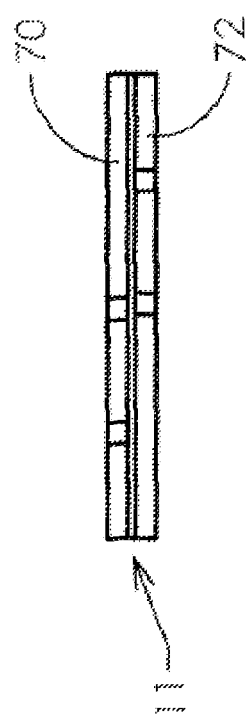
FIG. 6A is a side elevation plan view illustrating an embodiment of the electrolyzer/concentrator of FIG. 6.
Figure 6B:
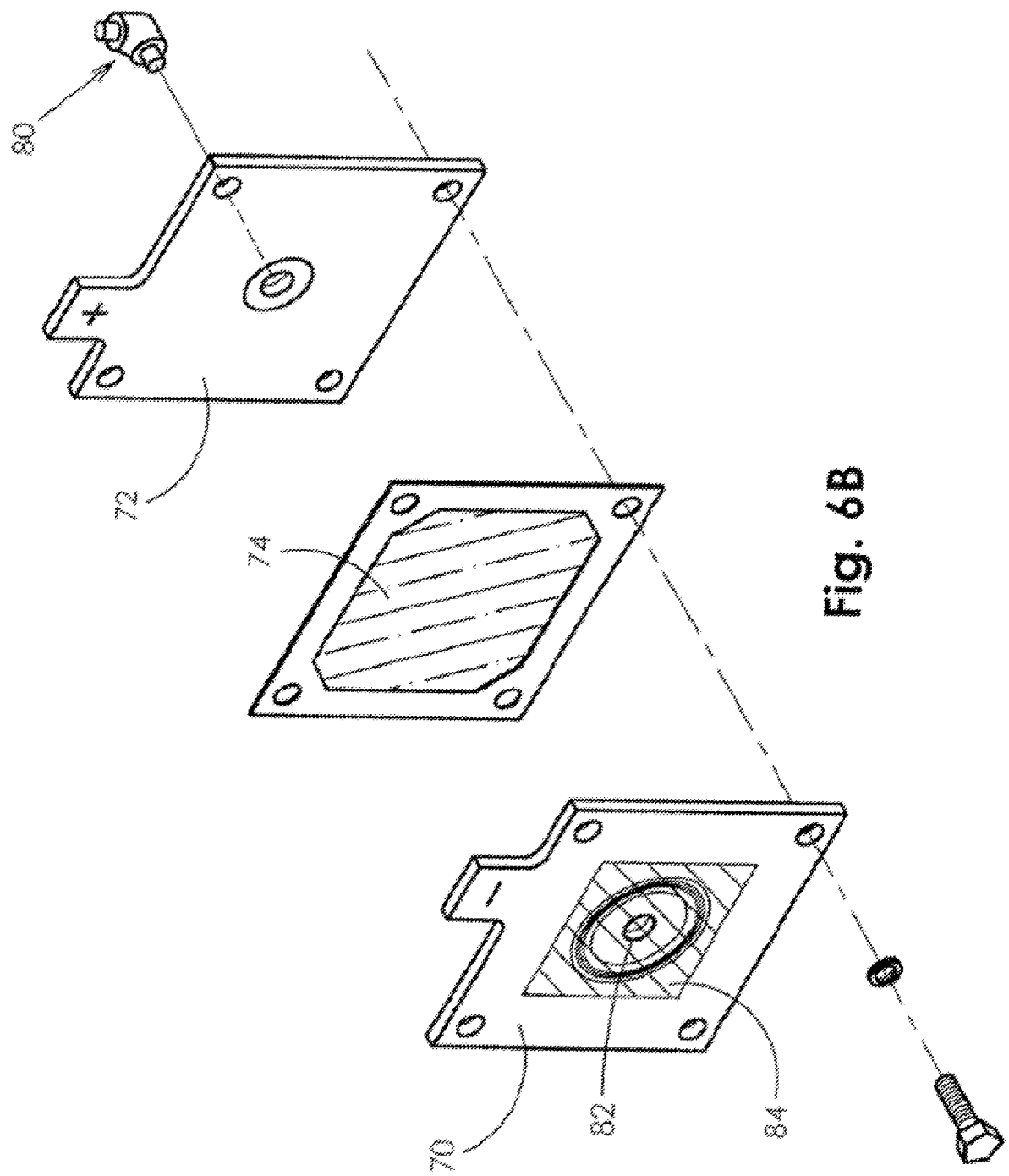
FIG. 6B is an exploded perspective view illustrating an embodiment of the electrolyzer/concentrator of FIG. 6.

Turning to FIGS. 6, 6A, and 6B, the electrochemical oxygen generator/concentrator 11 is illustrated. In the illustrated embodiment, the unique design of the concentrator provides a sturdier pumping unit. For example, there are times when the oxygen delivery tubing may become kinked or occluded, and in prior art concentrators, the concentrator would rupture as a result of any slight backpressure. The concentrator of the embodiments disclosed herein does not rupture when the discharge is occluded. In addition, the system is configured to provide alarms to notify the patient that the oxygen flow/pressure is out of range, thus allowing the patient to check the delivery tubing. If multiple tubings to multiple wound sites are provided, the system may provide alarms to notify the patient which of those tubings includes an oxygen flow/pressure that is out of range, thus allowing the patient to check which of the plurality of delivery tubings triggered the alarm. When a blockage of the oxygen flow occurs, an audible alarm may sound and, in some embodiments, a visual warning light may illuminate. For example, the alarm may sound for two minutes. In an embodiment, the alarm may be muted by pressing a mute button on the monitoring housing, which may operate to mute the audible alarm for fifteen minutes while the user troubleshoots the system, which may include inspecting the tubing for kinks or objects pressing on the tubing, or occlusion that may have occurred at the wound site under the dressing.

FIG. 6 is a top plan view of concentrator 11 showing the cathode plate 70 overlaying the anode plate 72. FIG. 6A is a side elevation view of the concentrator 11. Each of the charged plates may include a carbon backed metalized substrate with an 0.85 sq. inch titanium mesh plated on the woven fiber carbon membrane, which may provide a complete coverage area for electrical conductance to a NAFION® oxygen transfer membrane (NAFION® is a registered trademark of DuPont and is a sulfonated tetrafluroethylene copolymer that is well known in the art as a proton conductor for proton exchange membranes (PEMs)).

FIG. 6B is an exploded perspective view of the concentrator 11. The PEM membrane 74 may be compressed fully between the cathode 70 and the anode 72 by torquing screw type fasteners. An elbow 80 may be attached to the anode plate 72. Electrical contact and transfer to the plates may be accomplished by attaching a copper strip to the titanium mesh substrate. The compressive force applied may provide the necessary adhesion to the surfaces of the two metals. The strips may then be attached to the charge plates with epoxy.

Ambient air may enter the concentrator through inlet 82 which is covered by a filter membrane 84 that allows water vapor and gases to pass through, while preventing contaminants from entering the concentrator. Concentrated O2 may then be discharged out discharge valve 80 which communicates with a discharge outlet in housing 13.

Figure 7:
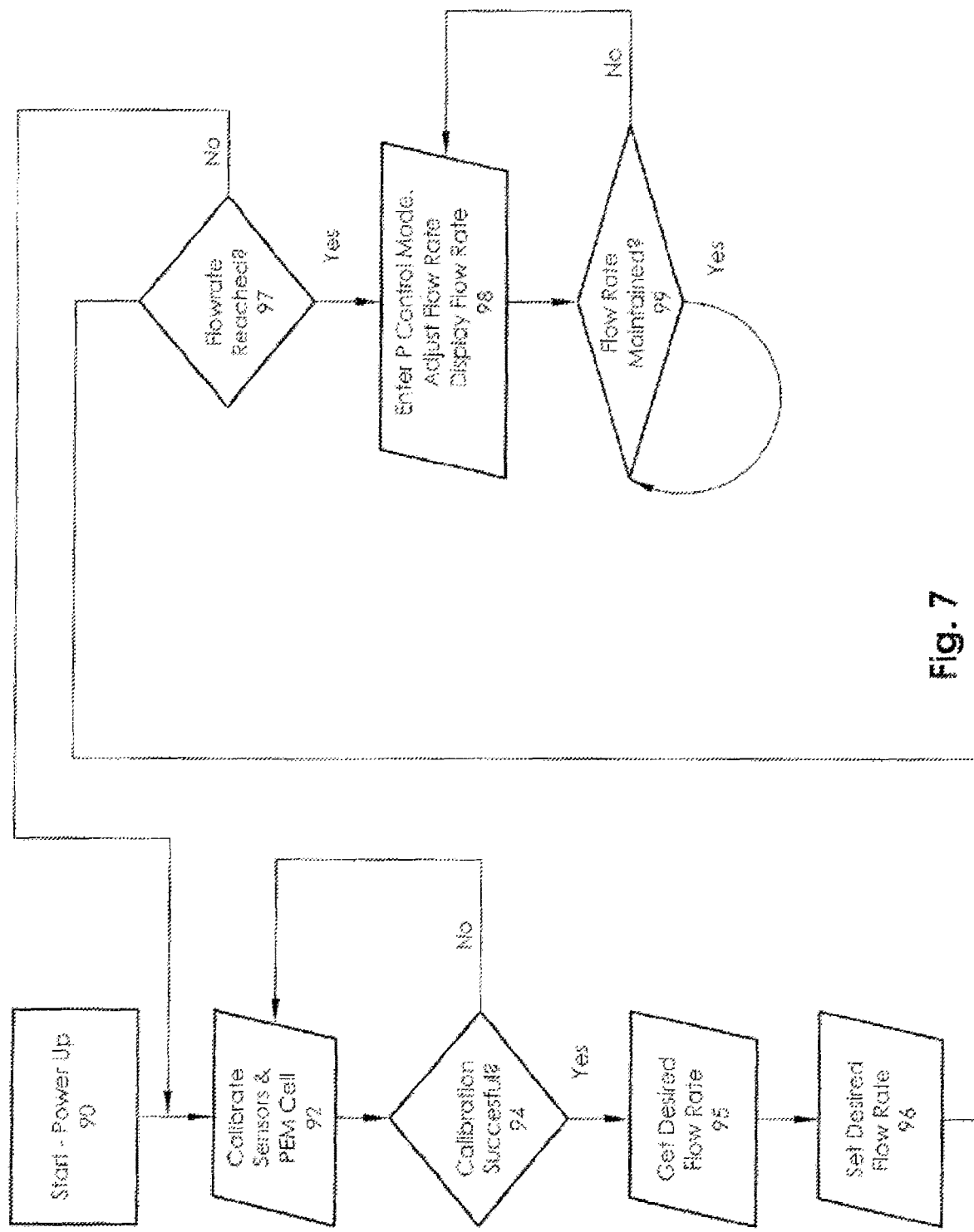
FIG. 7 is a flow chart illustrating an embodiment of a method for controlling tissue oxygenation that may be used with the tissue oxygenation system of FIG. 1.

FIG. 7 illustrates a flow chart of a method for controlling tissue oxygenation using the systems discussed above. When the monitoring unit 10 is started or powered up at block 90, the microprocessor 58 may calibrate all sensors and the PEM cell at block 92. Because every PEM cell and each sensor has its own particular functional characteristics, embodiments described herein calibrate the sensors and cell to ensure precise flow rates.

If the calibration is successful at block 94, the microprocessor may then retrieve the desired flow rate at block 95 from the user. In one embodiment, the desired flow rate may be received remotely from a caregiver (e.g., a doctor or nurse of the patient) or a manufacturer of the monitoring unit 10. The microprocessor may then calculate current to output from the PEM to set a desired flow rate at block 96. The microprocessor may then receive input from the flow rate sensor 54 and determines if the set flow rate has been reached at block 97 and, if not, the processor may again seeks to vary current to the sensors and the PEM cell. If the set flow rate is reached at block 97, then the microprocessor may enters a PID control mode at block 98. The flow rate may then be adjusted based upon input from the pressure monitoring system and flow sensors. The microprocessor may also display the flow rate and the temperature (where appropriate) on the monitor display screen 68. In a proportional control mode, the microprocessor may continuously tests the actual flow rate to ensure that it is maintained at block 99 using a feedback loop which looks at variations in sensor and PEM cell efficiencies.

In one embodiment, the flow rate may be adjustable up to a set ceiling, which may provide for a relatively high flow rate. For example, the flow rate may be set to such relatively high levels to treat entire limbs or portions of a patient's body, which may require flow rates in excess of several hundred ml/hr. In such embodiments, a flow rate of 100 ml/hr may be sufficient for a majority of applications, although higher flow rates are envisioned as falling within the scope of the present disclosure. In embodiments where multiple tubing is used to deliver oxygen to multiple wound sites, the flow rate to any particular tubing to particular wound site may be set to be different from that of tubing to other wound site, and may be based on the wound and/or wound characteristics. To achieve higher flow rates, the monitoring unit 10 may be provided with larger batteries or PEM cells to provide for a longer operating time between recharging. For example, the monitoring unit 10 may be provided with sufficient batteries to operate for 24 hours without recharging. In addition, multiple PEM cells or batteries may be placed in parallel to achieve a higher output flow rate where such flow rates are desired (e.g., for larger wounds, multiple wounds, etc.)

In some embodiments, a humidity pack may be provided with the concentrator 11 within the housing 13. In some examples, the humidity pack may be inserted into the monitoring unit 10 when a detected humidity is low (e.g., below a threshold), or may be present in the housing 13 and only activated when a detected humidity is low, or alternatively, may always be active to maintain a desired humidity within the housing 13. In some embodiments, the monitoring unit 10 may monitor the humidity of air to the fuel cell (i.e., the PEM cell), and may warn a user when humidity falls below a level which may potentially impact the function or efficiency of the device. For example, when humidity falls too low, the PEM cell may dry out and become less efficient, which may require additional power to achieve the same flow rate. Thus, if humidity is too low, the flow rate may decrease because there may be a limit as to how much power can be used to compensate for low humidity, and the humidity pack may be utilized to ensure proper humidity in the housing to prevent such occurrences.

In some embodiments, humidity packs may be provided as separate modules and in some instances may be attached to a battery pack. In some embodiments, the humidity pack is disposable and may be discarded after use. In other embodiments, the humidity pack may be rechargeable by adding water to the humidity pack. For example, a rechargeable humidity pack may include a separate recharging chamber from which water may be wicked as needed to recharge the humidity pack. As such, a monitoring or warning system may be included in the device to warn a user when humidity falls below a threshold via audible and/or visual signals, and that warning system may also use graphical, audible, or text instructions to assist a user with procedures to replace or recharge the humidity pack as discussed above, or with any associated troubleshooting as required.

In some embodiments, the battery of the monitoring unit 10 within the housing 13 is replaceable, while in other embodiments, the battery of the monitoring unit 10 within the housing 13 may be rechargeable.

In some embodiments, the processor of the monitoring unit 10 may record and report data to a manufacturer, a caregiver, and or any other entity that is related to the patient, the device, the use of the device, and/or any other information generated as discussed above. For example, the monitoring unit 10 may record and report any or all of: a patient's compliance with offloading, a patient's compliance with changing a wound dressing, compliance with proper connection of the tubing to the dressing, compliance with application of the dressing to the wound, and/or other compliance information known in the art. Furthermore, activity levels of the patient may be recorded. Further still, state information of the monitoring unit 10 such as the time and duration of the monitoring unit 10 being on, whether the device is properly charged, performance of the device (e.g., efficiency, flow output, or other characteristics), environmental conditions (e.g., humidity or temperature), device location (e.g., determined using global positioning satellites (GPS), BLUETOOTH®, Wi-Fi, etc.), and/or other device state information known in the art may be recorded and reported.

In one embodiment, reporting alerts based on the recordation of data may be sent to the patient, a caregiver, a manufacturer of the device, and/or other entities as desired. In some embodiments, the reporting alerts may be sent depending on the severity of the recorded information. For example, for issues that cannot be rectified by the patient, such as device performance warnings, alerts may only be transmitted to the manufacturer of the device, who may be able to intervene if there are indications that a device may have become compromised and needs replacement. Similarly, if the wound monitoring system experiences issues that could affect the patient or the patient's behavior, such as compliance with offloading or dressing changes, alerts may be transmitted to the patient and the caregiver, allowing either the patient or the caregiver (or both) to intervene earlier to ensure optimal outcomes. In some embodiments, congratulatory or encouraging notices or alerts may be sent to the patient if the patient is complying with caregiver or device recommendations, enforcing and ensuring the patient's future compliance. As such, any information recorded and/or reported may be analyzed by the device or another system in order to determine whether alerts or other reporting should be sent to any entities.

In accordance with some embodiments, the wound monitoring system or the monitoring unit may include communication capabilities provided by a communication device 70 such as, for example, a GSM or LTE cellular communication device. Additionally, the wound monitoring system or monitoring unit having a communication device 70 that may include a Wi-Fi (e.g., 802.11 a/b/c/d/n) communication device. The wound monitoring system or monitoring unit may also include near field communication or other radio frequency communication capabilities, such as BLUETOOTH®, to enable close-range data transmission between the wound monitoring system or monitoring unit and other devices, such as a patient's or caregiver's mobile telephone or other computing system.

The wound monitoring system or monitoring unit may include various power control features implemented by the power management system 52. In an embodiment, the monitoring unit may remain powered on once activated, and may require a specific override from a patient to power off the device. For example, the specific override may include a different button for turning off the device than is used to turn the device on. In another example, the monitoring unit may request confirmation from the patient to power the device off. In yet another example, the monitoring unit may require the patient to depress a power off button for a duration of time (e.g., two seconds) before the device is powered off. While a few examples have been provided, a variety of other power control features are envisioned as falling within the scope of the present disclosure.

Other control features may also be included in some embodiments of the wound monitoring system or monitoring unit. In an embodiment, if the system includes a communication device which connects the system to a network, the wound monitoring system may be remotely powered on, powered off, and controlled in a variety of manners. For example, the wound monitoring system may be turned off remotely to enforce payment requirements that allow for the use of the device, e.g., if a patient associated with the device has not provided sufficient payment for the device or ongoing rental of the device. In another example, the wound monitoring system may be turned off remotely if the device is reported as lost or stolen. In some embodiments, the manufacturer of the device or a caregiver may require periodic communication with the wound monitoring system to ensure compliance or authorization for continued use. For example, if too much time has elapsed from a previous communication with the device, the device may be remotely deactivated as a precaution. In another example, the device can also be remotely rebooted or power cycled for troubleshooting by technicians or the manufacturer.

In some embodiments, the wound monitoring system or monitoring unit further includes a relative humidity sensor that may facilitate the monitoring of relative humidity levels which may, in some situations, be used to trigger various other events such as the activation of a humidity pack, the sending of diagnostic data or performance data collected by the device, the requesting of assistance from a caregiver or manufacturer, the provision of warning signals to the patient, caregiver, or manufacturer, and/or other alerts or events known in the art.

In some embodiments, the monitor display screen 68 may provide additional information to the patient or caregiver such as, for example, feedback information. For example, feedback information may include automated warnings from the device such as low battery warnings, blockage warnings, low humidity warnings, etc.; information from the manufacturer such as server-side feedback, or customer service-type feedback such as positive reinforcement for compliance with instructions, warnings of potential issues (e.g., when the tubing or dressing is not properly connected), non-compliance warnings, and/or other feedback information known in the art.

In some embodiments, additional components, devices, or sensors may be used for temperature sensing or detection in addition to the temperature sensors that may be provided within the tubing as discussed above. For example, thermocouples, thermistors, wheatstone bridges, and/or other temperature measuring subsystems may be provided within or coupled to the monitoring unit 10. Such temperature measuring subsystems may be incorporated into the wound dressing, external to the housing, and/or coupled to the patient away from the wound site. For example, separate temperature measuring subsystems may be placed directly into a wound bed, inserted into a wound tunnel, or placed above a dressing material, such as in a non-adherent layer of the dressing. Additionally, for separate temperature measuring subsystems, a notation or other indication may be made in the memory of the device as to the location of the temperature measuring subsystem to permit tracking and reporting of potential temperature offsets from the wound site that may be determined based on the different locations of the temperature measuring subsystems. In some embodiments, the microprocessor or other component of the device may include the capability to detect different types of dressing or temperature measuring subsystems that have been attached to the device.

In some embodiments, the temperature measuring subsystems may be provided in the form of a flat tape, a small bulb, a rod, or other temperature measuring subsystem configurations known in the art. Such temperature measuring subsystems may be used to generate temperature measuring sensor data may be used to monitor wounds for changes in average temperature over time, which in some cases may indicate changes in the healing status of the wound. For example, infection or new capillary growth may be evident from temperature changes. Temperature data may also be used to monitor patient compliance, such as whether the dressing or temperature measuring sensor is placed properly on the wound (or placed on the wound at all), how frequently the dressing is changed, whether the patient is opening the dressing frequently to look at the wound, and/or other compliance related events known in the art. In one embodiment, the data from the temperature measuring sensor may be combined with data from any of the other sensors discussed above (e.g., perfusion data, pH data, pressure data, etc.) to refine analysis as to patient compliance, wound status, and/or other factors.

In some embodiments, additional components, devices, or sensors other than those discussed above may be used to detect pH levels. For example, pH sensors may be provided that are independent from a wound dressing as well as incorporated into the wound dressing. Such pH sensors may be placed directly into a wound bed, inserted into a wound tunnel, or placed above dressing material, such as in a non-adherent layer. In some embodiments, notations or other indication may be made in the memory of the device as to the location of the different pH sensor to permit tracking of potential offsets due to the different locations of the pH sensors. For example, if a pH sensor is incorporated into a wound dressing, the type of dressing and type of pH sensor may be entered into a memory of the device. In some embodiments, the device may include the capability to detect different types of dressings or pH sensor that have been attached to the device.

In some embodiments, the pH sensor may be provided as a flat tape, a small bulb, a rod, or other pH sensor configurations known in the art. The pH sensor data may be used to monitor wounds for changes in pH level over time, which may indicate a change in healing status of the wound. For example, pH changes may indicate new capillary growth or infection. Additionally, data from a pH sensor may be used to monitor patient compliance, such as whether the dressing or pH sensor is placed properly on the wound (or placed on the wound at all.) For example, a pH sensor may require liquid to function, and may provide a different output if the wound is dried out. Data from the pH sensor may also be used to determine the frequency of wound cleansing, and/or may be combined with data from temperature, perfusion, or pressure probes or sensors to further refine determination of patient compliance or wound status analysis.

In some embodiments, additional components, devices, or sensors may be used to monitor perfusion levels. Perfusion monitoring may include methods of detecting the relative and/or absolute amount of blood flowing into a wound, and in some embodiments may further include detecting the relative and/or absolute oxygen saturation of tissue in the wound bed. For example, a perfusion monitoring sensor may include a reflective photoplethysmograph. Similarly to the temperature monitoring sensors and the pH sensors described above, the perfusion monitoring sensor may be independent from a wound dressing as well as incorporated into a wound dressing. For example, a separate perfusion monitoring sensor may be placed directly into a wound bed, inserted into a wound tunnel, or placed above a dressing material, such as in a non-adherent layer. Additionally, a notation or other indication may be made in the memory of the device as to the location of different perfusion monitoring sensors to permit tracking of potential perfusion offsets from the wound site due to the different locations of the perfusion monitoring sensor. In one embodiment, the microprocessor or other component of the device may include the capability to detect different types of dressings or perfusion monitoring sensors that have been attached to the device.

In some embodiments, the perfusion monitoring sensor may have the form of a flat tape, a small bulb, a rod, or other perfusion monitoring sensor configurations known in the art. The perfusion monitoring sensor data may be used to monitor wounds for changes in wound perfusion over time, which in some cases may indicate changes in the healing status of the wound. For example, infection or new capillary growth may be evident from perfusion changes. Perfusion data may also be used to monitor patient compliance, such as whether the dressing or perfusion monitoring sensor is placed properly on the wound (or placed on the wound at all), how frequently the dressing is changed, whether the patient is opening the dressing to look at the wound, and/or other compliance related events. In some embodiments, the data from the perfusion monitoring sensor may be combined with data from other sensors, such as the temperature data, pH data, or pressure data discussed above to further refine determination of patient compliance or wound status analysis.

As such, the wound monitoring system allows patient data and therapy commands to be communicated between the device and a care giver or patient for processing by means of a data input key pad 64 and function control buttons 65. A data port 66 may be used to upload or download data. The monitoring system allows for collection and monitoring of key medical parameters to aid the caregiver in managing the patient care and potentially accelerate the healing process with improved access to more data. Available patient data and device functions are displayed and where appropriate are visually and audibly alarmed on the device function display screen 68. A digital camera 69 may also be utilized to aid the monitoring process visually tracking the wound closure progress.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A wound treatment system, comprising:
   a chassis;
   a processor that is located in the chassis; and
   a memory that is located in the chassis and coupled to the processor, wherein the memory includes instructions that, when executed by the processor, cause the processor to perform operations including:
   receiving environment information from a monitoring system that is indicative of an environmental characteristic in a restricted airflow enclosure provided by a dressing and located adjacent a wound site; and
   using the environment information to control power provided from a power delivery system to an oxygen concentrator in order to control an oxygen flow created by the oxygen concentrator and provided through at least one oxygen outlet to the restricted airflow enclosure.

2. The wound treatment system of claim 1, wherein the environment information that is indicative of the environmental characteristic in the restricted airflow enclosure includes pressure information indicative of a pressure in the restricted airflow enclosure.

3. The wound treatment system of claim 1, wherein the environment information that is indicative of the environmental characteristic in the restricted airflow enclosure includes pH information indicative of a pH in the restricted airflow enclosure.

4. The wound treatment system of claim 1, wherein the environment information that is indicative of the environmental characteristic in the restricted airflow enclosure includes perfusion information indicative of a prefusion perfusion level in the restricted airflow enclosure.

5. The wound treatment system of claim 1, wherein the environment information that is indicative of the environmental characteristic in the restricted airflow enclosure includes temperature information indicative of a temperature in the restricted airflow enclosure.

6. The wound treatment system of claim 1, wherein the environment information that is indicative of the environmental characteristic in the restricted airflow enclosure includes humidity information indicative of a humidity in the restricted airflow enclosure.

7. The wound treatment system of claim 1, further comprising:
a communications device coupled to the processor, wherein the operations include:
transmitting information via the communications device.

8. A non-transitory, computer-readable medium storing computer-readable instructions that, when executed by a processor, cause the processor to perform operations comprising:
receiving environment information from a monitoring system that is indicative of an environmental characteristic in a restricted airflow enclosure provided by a dressing and located adjacent a wound site; and
using the environment information to control power provided from a power delivery system to an oxygen concentrator in order to control an oxygen flow created by the oxygen concentrator and provided through at least one oxygen outlet to the restricted airflow enclosure.

9. The non-transitory, computer-readable medium of claim 8, wherein the environment information that is indicative of the environmental characteristic in the restricted airflow enclosure includes pressure information indicative of a pressure in the restricted airflow enclosure.

10. The non-transitory, computer-readable medium of claim 8, wherein the environment information that is indicative of the environmental characteristic in the restricted airflow enclosure includes pH information indicative of a pH in the restricted airflow enclosure.

11. The non-transitory, computer-readable medium of claim 8, wherein the environment information that is indicative of the environmental characteristic in the restricted airflow enclosure includes perfusion information indicative of a perfusion level in the restricted airflow enclosure.

12. The non-transitory, computer-readable medium of claim 8, wherein the environment information that is indicative of the environmental characteristic in the restricted airflow enclosure includes temperature information indicative of a temperature in the restricted airflow enclosure.

13. The non-transitory, computer-readable medium of claim 8, wherein the environment information that is indicative of the environmental characteristic in the restricted airflow enclosure includes humidity information indicative of a humidity in the restricted airflow enclosure.

14. The non-transitory, computer-readable medium of claim 8, wherein the operations include:
transmitting information via a communications device.

15. A method for treating a wound, comprising:
receiving, by a processor, environment information from a monitoring system that is indicative of an environmental characteristic in a restricted airflow enclosure provided by a dressing and located adjacent a wound site; and
using, by the processor, the environment information to control power provided from a power delivery system to an oxygen concentrator in order to control an oxygen flow created by the oxygen concentrator and provided through at least one oxygen outlet to the restricted airflow enclosure.

16. The method of claim 15, wherein the environment information that is indicative of the environmental characteristic in the restricted airflow enclosure includes pressure information indicative of a pressure in the restricted airflow enclosure.

17. The method of claim 15, wherein the environment information that is indicative of the environmental characteristic in the restricted airflow enclosure includes pH information indicative of a pH in the restricted airflow enclosure.

18. The method of claim 15, wherein the environment information that is indicative of the environmental characteristic in the restricted airflow enclosure includes perfusion information indicative of a perfusion level in the restricted airflow enclosure.

19. The method of claim 15, wherein the environment information that is indicative of the environmental characteristic in the restricted airflow enclosure includes temperature information indicative of a temperature in the restricted airflow enclosure.

20. The method of claim 15, wherein the environment information that is indicative of the environmental characteristic in the restricted airflow enclosure includes humidity information indicative of a humidity in the restricted airflow enclosure.

* * * * *

UNITED STATES PATENT AND TRADEMARK OFFICE
CERTIFICATE OF CORRECTION

| | | |
|---|---|---|
| PATENT NO. | : 11,529,503 B2 | Page 1 of 1 |
| APPLICATION NO. | : 16/298294 | |
| DATED | : December 20, 2022 | |
| INVENTOR(S) | : Michael C. Wells et al. | |

It is certified that error appears in the above-identified patent and that said Letters Patent is hereby corrected as shown below:

In the Claims

In Column 15, Line one, please delete "prefusion".

Signed and Sealed this
Twenty-eighth Day of February, 2023

Katherine Kelly Vidal
*Director of the United States Patent and Trademark Office*